United States Patent [19]

Tobolski et al.

[11] Patent Number: 4,667,509
[45] Date of Patent: May 26, 1987

[54] DIGITAL TESTER FOR MEASURING THE HARDNESS OF THE MATERIAL

[75] Inventors: Edward Tobolski, Beacon Falls; Ronald F. Grosso, Shelton; Joseph Cieplak, Northford; Elliot Lang, Hamden, all of Conn.; Ralph Hershberger, Philadelphia, Pa.

[73] Assignee: Page-Wilson Corporation, Bridgeport, Conn.

[21] Appl. No.: 856,866

[22] Filed: Apr. 24, 1986

Related U.S. Application Data

[63] Continuation of Ser. No. 585,162, Mar. 1, 1984, abandoned.

[51] Int. Cl.4 .............................................. G01N 3/44
[52] U.S. Cl. ........................................................ 73/83
[58] Field of Search ...................................... 73/81, 83

[56] References Cited

U.S. PATENT DOCUMENTS

| | | | |
|---|---|---|---|
| 3,123,998 | 3/1964 | Newman | 73/83 |
| 4,182,164 | 1/1980 | Fohey | 73/83 |
| 4,245,496 | 1/1981 | Napetschnig | 73/83 |

Primary Examiner—Jerry W. Myracle
Assistant Examiner—John E. Chapman, Jr.
Attorney, Agent, or Firm—Peter L. Berger

[57] ABSTRACT

An automatic tester for the hardness of materials is disclosed in which the operations are automated and in which the possibility of human error is significantly eliminated. Particularly, a linear digital encoder is employed which is attached to the capstan and elevating table arrangement. Pulses are developed according to the movement of the penetrator in the workpiece and are utilized to standardize and measure the time during which the major and minor loads are applied to the workpiece. Additionally, use of a CPU according to certain preset procedures and methods allows for enhanced reliability of the testing procedures. Conversions from different testing scales as well as corrections of certain factors is easily accomplished. Still further, the tester includes the provision to insure that certain ASTM standards are met by testing the device with standard test blocks and comparing results with those preset in the CPU.

12 Claims, 13 Drawing Figures

DIGITAL TESTER FOR MEASURING THE HARDNESS OF THE MATERIAL

This application is a continuation, of application Ser. No. 582,162, filed Mar. 1, 1984, abandoned

BACKGROUND OF THE INVENTION

This invention relates to an apparatus for measuring the hardness of materials by measuring the difference in penetration of a penetrator under minor and major loads, for example in testing devices for Rockwell tests.

Hardness testing devices have been widely sold for many years. These devices are utilized to determine the hardness of a material, and one conventional procedure for determining such hardness is to determine the difference in penetration of a tip under minor and major loads. These test procedures have been largely performed by skilled personnel over many years, and the sensitivity or experience of the operator largely contributes to the quality and value of the test results.

Unfortunately, such human factors which materially affect the conducting of such hardness tests are undesirable, because of the differences between operators and the increasing difficulty to develop and find personnel who are qualified and trained to perform such tests.

Digital readers for displaying the results hardness tests have been widely employed in such testers, but relatively foolproof and fail-safe measurement techniques are not generally available.

Hardness tests are conducted which relate to a variety of standard scales. Although a measurement can be made and a display produced in one scale, it may be necessary for the operator to be able to quickly determine the reading in another scale. This is generally done by the operator consulting various tables and converting the reading in one scale to that in another scale. Such human conversion often is fraught with errors, and the ability to reliably convert the reading from one scale to another is not readily available and can be time consuming.

Sometimes as the minor load is applied by raising the elevating screw to have the workpiece contact the penetrator, the motion of the elevating screw is reversed. This reversal of direction as the minor load is being applied causes inaccuracies to develop in the measurement process. It is desirable that measurements not be made when there has been such direction reversal to prevent an invalid measurement to be made. In the past, such reversals of the elevating screw would only be known by the operator, and there would be no way for anyone else to know whether or not the test was properly conducted.

As the minor load is applied, sometimes the elevating screw moves too far causing an overload or overset for the minor load. Here again, due to the human element in the measurement procedures, such overset will only be known by the operator, and the measurement can proceed producing invalid data.

It is important to standardize the measuring procedures from machine to machine. One of the most critical aspects of the test procedure is the rate of application of the major load to the workpiece. Such rate control is not controlled from machine to machine, and this factor contributes to a lack of standardization between machines. This can lead to inaccuracy and unreliability in the hardness measurements, and it is an undesirable aspect of hardness testers.

The hardness measuring procedures described above are generally manually controlled. The time at which the major or minor loads are to be applied and/or removed is generally dependent upon the operator's ability and experience. An important aspect of determining the hardness of the material being tested is to properly apply and remove the major and minor loads at the proper times in the procedures, so that an inaccurate measure of the hardness of the material under test is prevented.

Hardness tests are performed according to certain ASTM standards. These standards relate to the type of materials being tested. Additionally, certain ASTM standards apply to metals, plastics and other types of materials, and in order to determine the proper standards, the operator must consult various tables prior to the test procedure. Clearly, the likelihood of human error is always present, and improper ASTM standards can be applied during the test procedure resulting in inaccurate and unreliable measurements which may not be detected because one may not be able to know that the operator used incorrect standards.

Another aspect of the prior art hardness testers relates to the choices of the major load, minor load and penetrator tip. The load to be applied as well as the penetrator tip relates to the scale and the type of test being employed. For a superficial test, lower major and minor loads are used, but this may not be followed when the measurement is run because manual selection of the proper load and tip is required.

The shape of the material being tested is an important factor in its hardness reading. If the material being tested is cylindrical, there are certain correction factors, such as the inside and outside diameters of the workpiece, and these factors must be considered in the test results. Here again, the operator must consult separate tables, and hopefully, if the operator correctly finds the proper point and the proper tables and then makes the proper corrections, an accurate measurement will be provided. Unfortunately, often there are human errors in this process, and the correction for the cylindrical shape of the device is not properly made.

Certain parts are regularly tested for hardness. Each time the part is to be tested, the operator determines the appropriate test procedures, the proper loads and the proper standards. Here again, the operator's subjectivity could lead to incorrect measurements of the material being tested.

Certain operators may find difficulty in consulting and working with various printed tables and in following specific instructions. The ability to provide a multisensory set of instructions, standards and procedures to the operator can materially enhance the validity and reliability of the test procedures.

Although certain prior hardness testers provide digital readouts, there is, as yet, no reliable prior art devices in which information and data are stored to be used during test operations. For product reliability standards as well as historical data, such a facility would be desirable, and this is unavailable in the prior art.

An object of this invention is to provide an improved tester for measuring the hardness of the materials.

Still another object of this invention is to provide such a tester in which the human error encountered in prior art devices is substantially eliminated.

Another object of this invention is to provide the operator the ability to automatically convert from one test scale to another test scale and reliably display the test in any desired scale.

Yet another object of this invention is to insure that the test procedure is performed properly and inhibit the test if there is an overset in the application of the minor load or a reversal of the movement of the elevating screw.

Another object of this invention is to provide a multi-sensory facility to provide both voice and visual information including standards and operating procedures so that the operator more reliably will follow the proper tests according to direction.

Another object of this invention is to effectively determine the exact time at which the major load is to be applied and to be removed, and to determine the proper time at which the hardness measurement is to be made.

Still another object of this invention is to provide such a tester in which the ability to automatically correct for material variations and shape is effectively and automatically incorporated within the apparatus, such that the operator need merely insert data to automatically correct for that inserted data.

Another object of this invention is to provide a tester in which for certain parts which are recurrently tested, the machine will automatically detect and sense the proper operating test procedures and conditions to minimize human error.

Yet another object of this invention is to provide an apparatus in which the proper minor and major loads as well as the penetrator type is displayed to the operator according to the scale in which the test is to be made.

Another object of this invention is to insure that the tester operates within proper standards, and this is accomplished by utilizing standard test blocks and running the tests to compare the results with standard ASTM standards for those blocks for such reliability checks.

Yet another object of this invention is to provide a data storage and display apparatus in which the statistical data relating to the tests can be effectively stored, retrieved and utilized for various aspects in the testing operations.

Yet another object of this invention is to provide such a test apparatus in which the ability to convert to a measurement in one scale from another and display the same is readily accomplished by automatically displaying and scrolling to the desired scale according to information entered into the machine.

Other objects, advantages and features of this invention will become more apparent from the following description.

SUMMARY OF THE INVENTION

In accordance with the principles of this invention, the above objects are accomplished by providing an automatic hardness tester in which a digital processor is employed to control and reliably effect measurements eliminating the element of operator error. In particular, the tester includes an encoder which is connected with the platform on which the piece to be measured is carried, the encoder providing a plurality of signals relating to various aspects of the measurement process. Prior to applying the minor load, the measurement scale is selected and keyed in. The central processor determines the proper loads to be employed as well as the penetrator to be utilized. The material to be tested is initially placed on the platform and an elevating screw is employed to lift the piece to apply the minor load. This elevating screw can be automatically operated and as the minor load is being applied, the encoder issues a series of pulses which are utilized to determine when the desired level for the minor load is reached.

The encoder provides directional signals indicating the direction of movement of the elevating screw and platform. If a reversal of movement is sensed, the measurement process will not be run. There will be no display of any measurements.

The tester includes the ability to determine the proper time to remove the major load and calculate the hardness. This is accomplished by providing a slope detector which senses the rate of movement of the penetrator into or out of the piece. When the rate reaches a selected level the measurements are completed, and the next operation occurs. This eliminates the human error related to selecting a proper time to remove the major load and calculate the hardness.

As another aspect of this invention, the slope detector determines the rate at which the major load is applied. As discussed above, it is important to have consistency between machines. Therefore, the machines include the ability to adjust the rate of application of the major load so that such rate is the same for all testers.

The utilization of the central processing unit allows for certain data to be preloaded into the tester and to ensure that the proper correction factors as well as shifting from scale to scale is efficiently achieved. The apparatus also includes the ability to store the relevant test procedures and standards for preselected parts which are regularly tested on the apparatus. This information is used to control the operating procedure and to instruct the operator during the test. Additionally, the present invention includes the provision of a visual and oral display to simultaneously instruct the operator as to the proper steps in conducting of the test procedures.

Additional details of the invention will become more apparent from the following description in which the tester is described in sufficient detail to enable one of ordinary skill in the art to practice the invention.

DETAILED DESCRIPTION OF THE DRAWINGS

Figure 1:
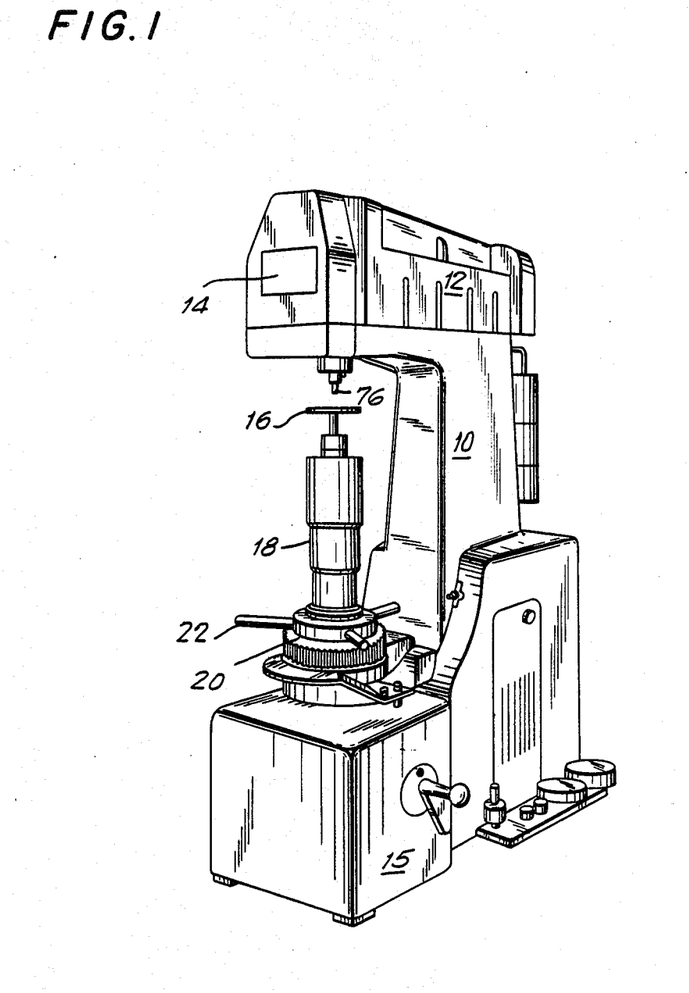
FIG. 1 is a perspective view of the tester of this invention.

FIG. 1 is a perspective view of the tester of this invention. The tester generally has a C shaped frame with a center vertical support or column 10 and an upper head section 12, the head section including a display panel and keys generally designated as 14. The bottom 15 of the unit rests on a support. The workpiece to be tested is placed on a platform 16 which is connected with a telescoping elevating unit 18 which is raised by the rotation of a capstan nut 20 located at the bottom of the elevating unit, the capstan nut including a plurality of handlebars 22. The perspective view of the hardness tester of this invention presents a relatively similar appearance to other prior art testers, although the operation of the present tester is materially different.

The ROCKWELL hardness of a material is determined by measuring the depth of an impression produced by a known shaped indenter that is forced into a sample under known load conditions. The measurement is actually a differential measurement of two depths. A small reference load called the "Minor" load is applied and the penetration of the indenter is measured. The full test load called the "Major" load is applied. It is then removed with the Minor load maintained and the second depth measurement is made. The difference of these two measurements is the depth of the impression.

There are two basic ROCKWELL hardness tests. One is called "Regular" and the other is called "Superficial". The regular scale always uses a 10 Kg Minor load and either a 60, 100 or 150 Kg Major load. The superficial scale uses a 3 Kg Minor load and a 15, 30 or 45 Kg Major load. The indenter is either a specially shaped diamond or a 1/16, ⅛, ¼ or ½" hardened steel ball. The proper choice of test, load and indenter is determined by the hardness and the thickness of the sample under test. The softer the material, the greater the depth of the impression, therefore, everything else equal, one would use a lighter load and a larger diameter indenter.

An infinitely hard sample, (no net penetration) would have a ROCKWELL hardness of 100 for the regular BRALE scales and all superficial scales. On the regular ball scales an infinitely hard sample would have a hardness of 130. As the material gets softer the hardness number decreases. The lowest readings that are used varies from ROCKWELL 20 on the 'C' scale to "0" on the ball scales.

On the regular ROCKWELL, 100 points of penetration is equal to 0.2 mm change in depth. On the superficial ROCKWELL scale, 100 points of penetration is equal to 0.1 mm change in depth. ROCKWELL hardness on digital machines is equal to 0.1 ROCKWELL points.

Figure 3:
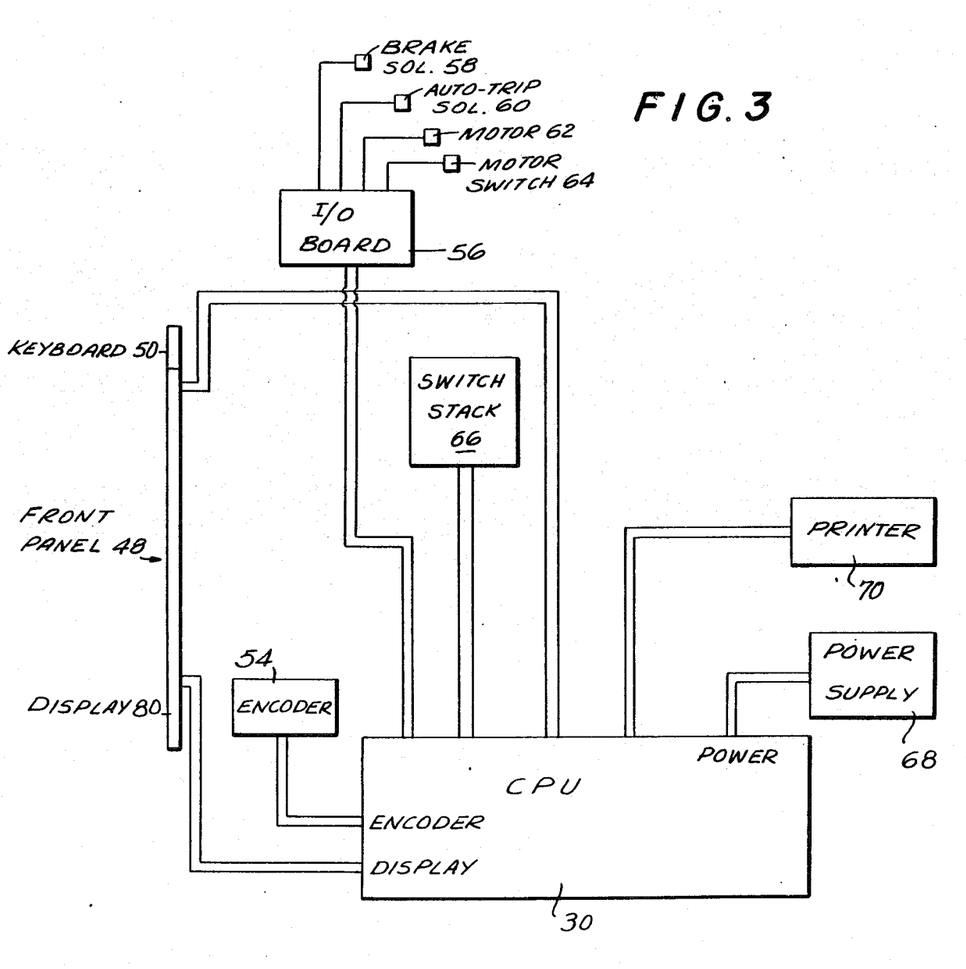
FIG. 3 is a block diagram of the control aspects of this invention.

FIG. 3 is an operative block diagram of the electronics of the present invention. The heart of this invention is a CPU central processing unit which is an Intel 8085 generally designated by the numeral 30. This unit has a plurality of output ports, and these are separately designated as the display 32, encoder 34, load 36, switches 38, keyboard 40, printer 42 and a power terminal 46. The display 32 is connected to the front panel 14. The keyboard identified as numeral 50 is connected to the CPU 30 by a connection cable 52.

The present invention includes a linear digital encoder 54 which may be a type manufactured by Dynamics Research Corp. of Massachusetts. This encoder has an excellent resolution which allows for effective and accurate measurements. The encoder is connected in the head 12 of the tester and senses movement of the penetrator by producing a series of pulses relating to the amount of such movement. In particular, the encoder has a resolution of 1 micron when used with regular Rockwell tests and 0.5 microns when used with superficial Rockwell tests. Higher resolution can be obtained by a suitable mechanical linkage to increase the sensitivity of the encoder.

The tester of this invention includes solenoids which operate related electro-mechanical elements. In particular, an input-/output board 56 is connected to the CPU 30 at the load terminal 36 and to a brake solenoid 58, an auto-trip solenoid 60, the elevating motor 62 and a motor switch 64.

A plurality of switches are controlled by the central processing unit 30, and these switches are connected together in a switch stack 66 which is connected to the CPU through switches terminal 38. A power supply 68 is connected to the power terminal 46 of the CPU unit 30 and terminal 42 is connected to a printer 70 to print the results of the tests.

Figure 2:
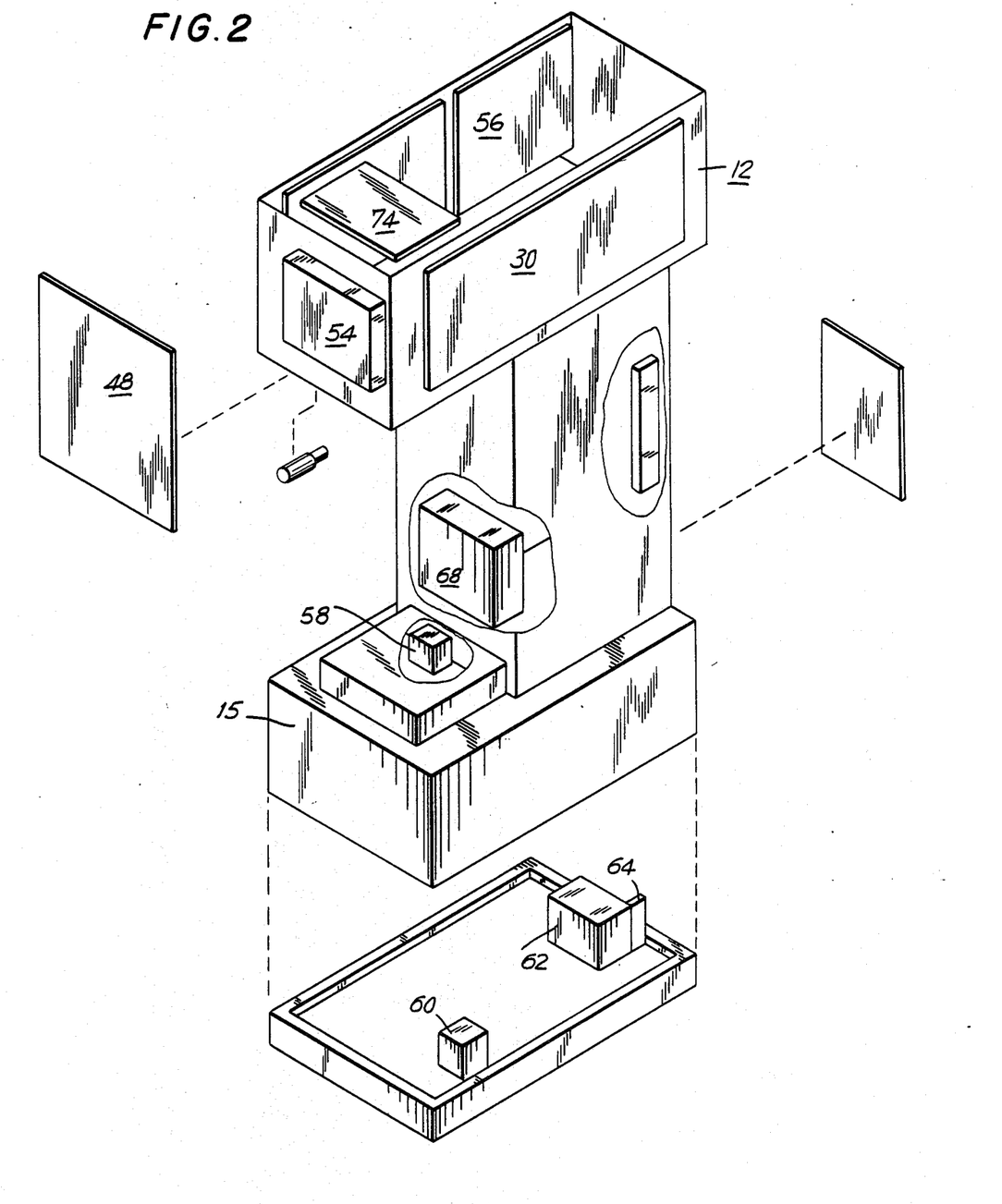
FIG. 2 is an exploded perspective view of the tester of FIG. 1 with the major components thereof illustrated.

FIG. 2 is an exploded perspective view of this invention. The base 15 is shown enclosing the motor 62, the motor switch 64, and the auto-trip solenoid 60. Brake solenoid 58 is carried at the base of the capstan unit, while the power supply 68 is housed and carried within the column 10 of the frame of the tester. The CPU 30 is located on a PC board and is attached at one side of the head of the frame, while additional PC boards including an encoder PC board 74 are also attached in the head of the tester. The linear digital encoder 54 is attached in the front of the head of the tester, and this encoder senses the upward or downward movement of the penetrator as the machine operates. The input/output PC board 56 is also mounted within the head of the unit, and the front panel and keyboard are attached to the front portion of the head 12 of this device.

A brief explanation of the general operation of the apparatus will now be set forth.

The operator rotates the capstan nut 20 by hand which raises the elevating unit 18 lifting the workpiece. As the workpiece contacts the penetrator 76, the minor load starts to be applied and the encoder 54 starts to count in one direction. After a preset number of counts, a solid state switch operates a solenoid 58 or a relay locking the nut at the proper minor load. Then another solid state switch operates actuating auto-trip solenoid 60 initiating the application of the major load. As the load is applied the encoder starts counting and the count is accumulated. As the major load is fully applied, the motion of the penetrator begins to stop, and the rate of movement of the penetrator as sensed by the encoder and the pulse rate will approach zero. When a predetermined rate is reached, the apparatus will energize another solid state switch 64 which after a preset delay will start motor 62 to remove the major load. As the major load is removed, the encoder 54 will issue pulses as though it were counting in the opposite direction. As the major load is being completely removed, again the motion tends to stop and the pulse rate will approach zero. At a predetermined rate, the hardness test is complete and the net count representing the depth and the results are displayed. Also, the capstan nut is released allowing the operator to manually lower the elevating unit 18. The operator then lowers the elevating unit 18 removing the sample. The motion of the penetrator stops at a fixed vertical position and the net counts of the motion will be zero.

Figure 12:
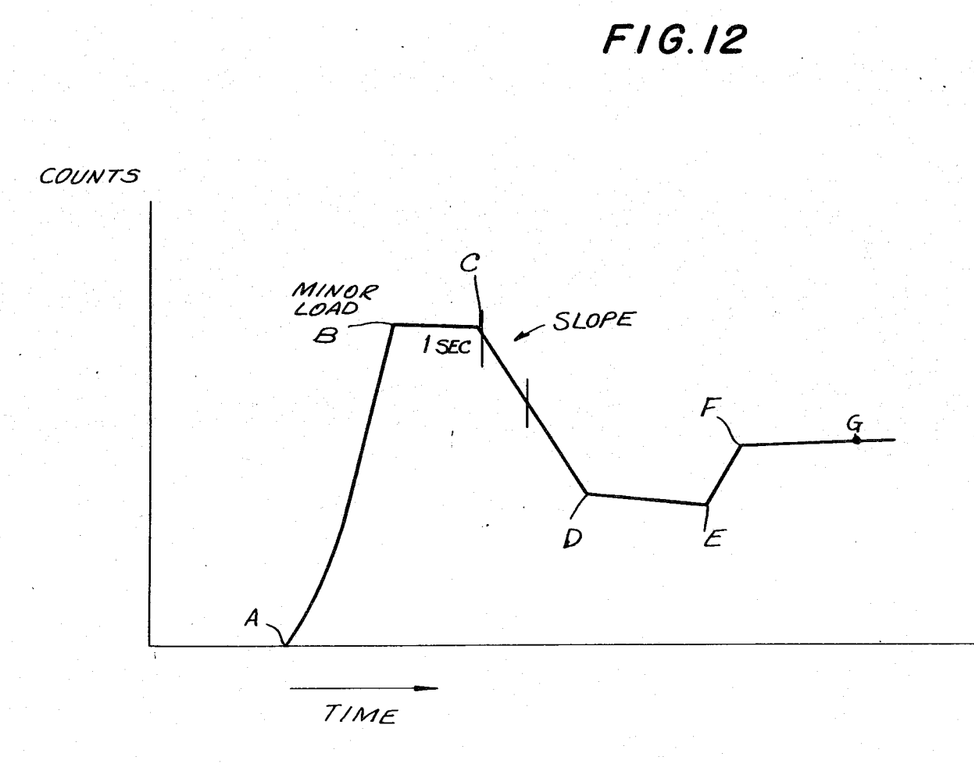
FIG. 12 is a curve illustrating the steps in the tester operation.

FIG. 12 is a curve showing the motion of the penetrator as the operation of the machine ensues.

The start position is indicated at point A and this is before the test begins to operate. As the capstan is rotated and the minor load begins to be applied, the movement of the penetrator is indicated to be upwardly directed and when a certain number of pulses are counted according to the operation of the linear encoder 54, the proper minor load will have been applied. This is at point B of the curve. A preset time delay is then included as part of the operation of the machine, and after the minor load is properly applied and the time delay is over, the tester begins to apply the major load. This commences at point C of the curve. As the major load is applied, it is applied at a certain rate. As the major load urges the diamond penetrator to the completion of its penetration into the piece being tested, the rate of application of the major load to the workpiece begins to slow down. At an appropriate rate of application of the major load, the operation will be terminated because the test will have been completed. This occurs at point D of the curve, and thereafter the major load will be allowed to come to rest during a certain dwell time which occurs between periods D and E. It should also be noted that as the major load is applied and the curve moves between points C and D, the rate of application of the major load can be determined, and a standardized measurement is developed in order to ensure similar application rates for different machines. This will be described in further detail hereinafter.

After the major load has been applied, and the dwell time has elapsed, the major load is removed from the workpiece. The rate of removal of the penetrator from the workpiece is also sensed according to the movement of the penetrator and the rate of production of pulses from the linear encoder 54, and when that rate decreases to a predetermined level, as at point F, it is determined that the measurement of the hardness is completed. The measurement is not actually made until after a certain recovery time, and that recovery time is determined in part by the material being tested. At the end of the recovery time, and as indicated at point G in the figure, a measurement is made as to the difference in penetration between points C and G, and that difference in penetration is a measure of the hardness of the material under test.

Figure 13:
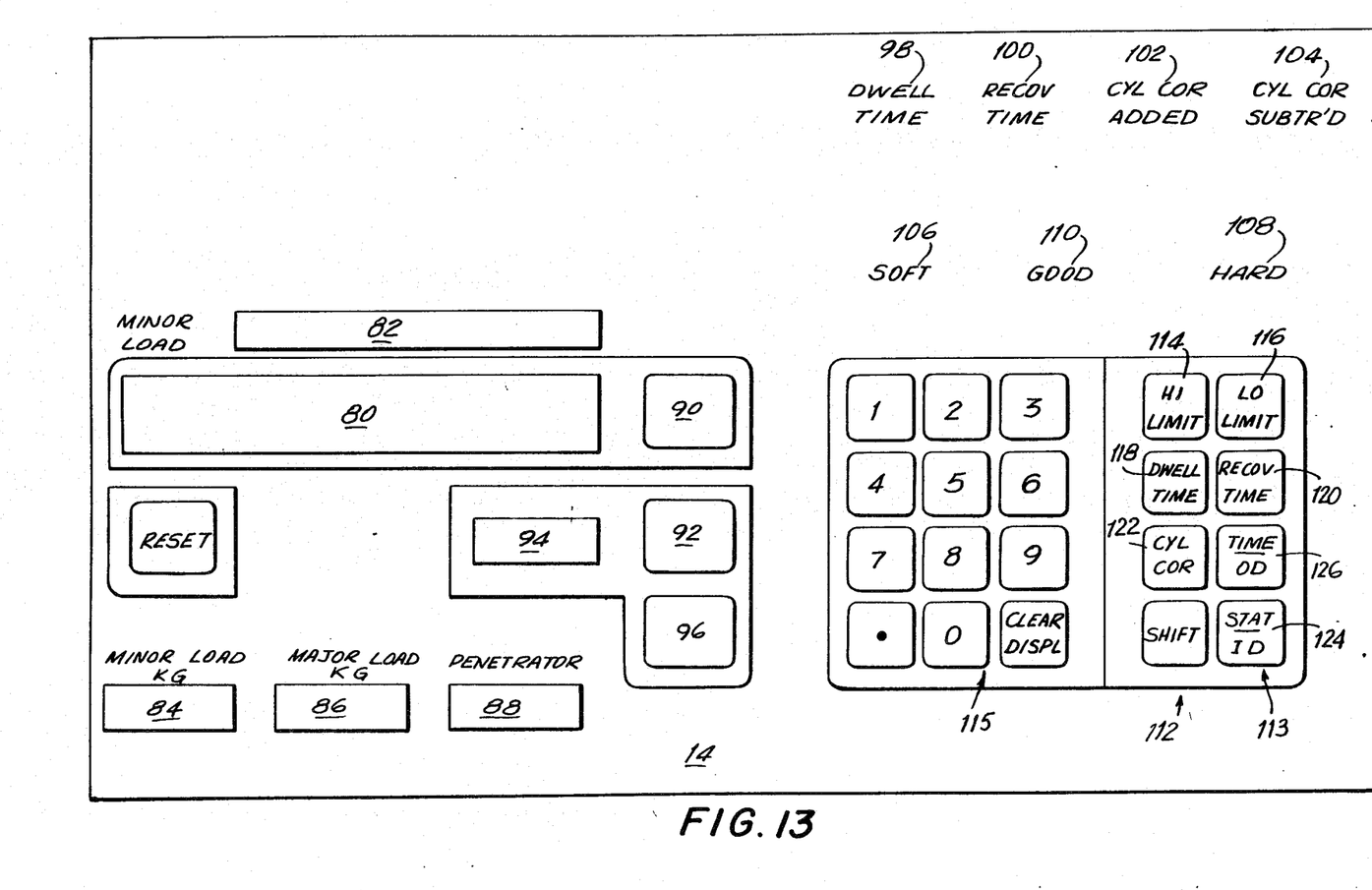
FIG. 13 is a front view of a display panel and operating keys of this invention.

FIG. 13 which had been briefly described above is an alternative embodiment of the display panel of this tester. This embodiment is an expanded version of that shown in FIG. 1. The results of the tests or the hardness or other factors relating to the measurements are displayed in a display readout window 80, and the amount of minor load being applied is displayed in a display readout window 82. The selection of the proper minor load, major load and penetrator is displayed in windows 84, 86 and 88, and these values are related to the proper test scale which will be utilized for the measurement. In particular, a test scale scroll key 90 is operated to scroll the various scales which could be used for the measurement, and at each scale scroll, the appropriate minor load, major load and penetrator will be displayed.

One of the features of this invention which will be described in more detail hereinafter relates to the ability to display the measurement in different scales. A conversion scroll key 92 is provided which will scroll the different scales under which the tests could be made. Even though the test might be made in a C-scale, the display could also indicate the reading in a D or G scale. The scale which is appropriate to the measurement identified in window 80 is simultaneously identified in window 94, and the conversion is accomplished by hitting the approx-conversion key 96.

Certain other aspects of the operation of the tester are also identified in the display panel. In particular, the dwell time is identified in window 98, the recovery time in window 100, the added cylindrical correction factor in window 102 or the subtracted factor in window 104. The type of material being tested is indicated in display windows 106 and 108 as being soft or hard, and window 110 indicates that the test has properly proceeded and a proper measurement has taken place.

An additional panel area 112 is provided which comprises a series of function 113 and numerical keys 115 with the function keys being depressed followed thereafter by depression of the appropriate numerical keys to input certain numerical data for the test procedures and display. In particular, the high and low limits can be manually set in by keying the appropriate numerical keys, and these settings will be displayed in display window 80. The high and low limits are set by first depressing the respective keys 114 and 116 and thereafter depressing the appropriate numerical keys. Additionally, the dwell and recovery time can also be set by the same procedure by using the respective keys 118 and 120. In order to correct the measurement for a cylindrical piece, a cylindrical key 122 is depressed, and the appropriate information is keyed in in addition to which the inside and outside diameters are also keyed in by using keys 124 and 126.

Window 80 is an alpha-numeric display which displays not only the above-described functions but also whether or not the machine is operating properly, in which mode it is operating according to the functions described with relation to the curve in FIG. 12, whether or not the tests should be conducted or voided and other information yet to be described.

The block diagram of the invention has been described above with relation to FIG. 3, and CPU 30 is a micro-processor which is capable of being organized to control different functions. This invention will be further described with regard to specific functions accomplished and organized by the CPU, although the specific software instructions will not be identified, since these will be obvious to one of ordinary skill in the art given the functions to be accomplished and the identification of the CPU.

Figure 4:
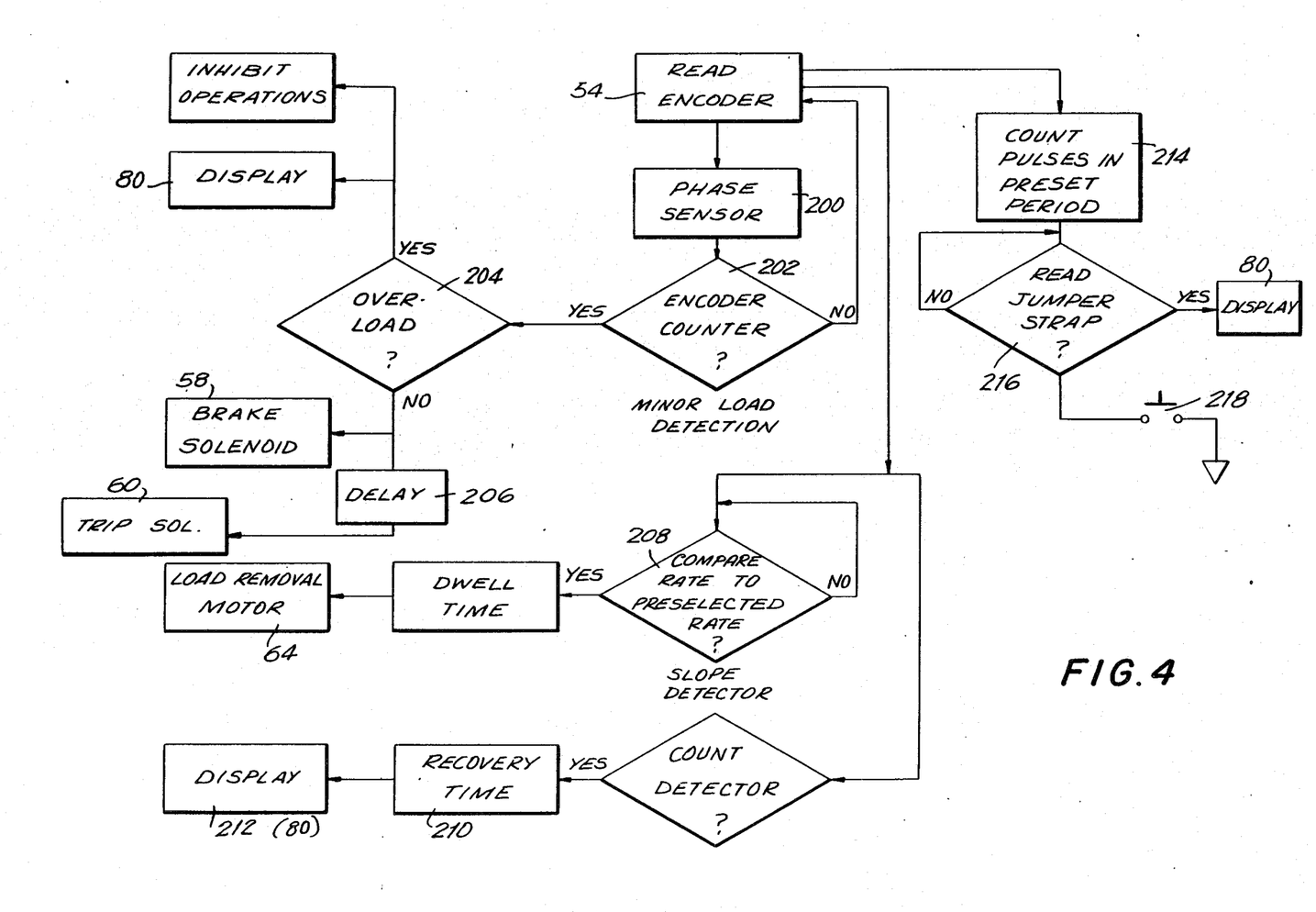
FIG. 4 is a flow chart illustrating the operation of the tester including the initial application of the minor load and sensing of the rate of application of the major load to the materials being tested.

FIG. 4 is a flow diagram in which the operation of several features of the invention is described. In particular, the encoder 54 produces counts which pass through a phase sensor 200. If the phase sensor senses a reversal of phase in the output of the signals from encoder 54, a signal will be emitted which will be supplied to the CPU which will terminate further measurement operations of the device.

This, of course, relates to a reversal of the elevating screw as the minor load is being applied. Additionally, display window 80 will indicate that such reversal has taken place and no test can proceed.

If the phase sensor does not indicate such a phase reversal, the encoder counter will count to a preset number, and that preset number will be related to the minor load to be applied to the workpiece. As long as that count is not reached, the encoder will continue to produce pulses supplied to the encoder counter 202. So long as the encoder counter continues to count, the encoder will continue to produce pulses. Once the preset count level is reached, a Yes indication is indicated, but if the total count exceeds an overset amount as identified in block 204, the entire operation will be aborted and no further measurements can take place. If a Yes is produced by the overset comparator 204 then a larger than desired minor load was applied, thus preventing the measuring operation from taking place.

As long as the encoder count is greater than the preset number but less than the overload, the operation will continue. At that point, the minor load will be considered as having been set, and locking solenoid 58 will be energized thereby ensuring that the minor load has been applied to the piece being tested. A preset delay is then initiated as illustrated in box 206, and thereafter, the major load begins to be applied to the piece being tested. This occurs by the passage of the preset delay in box 206 which then energizes auto-trip solenoid 60 to begin the application of the major load. At this point, read encoder 54 again begins to generate a series of pulses which relates to the movement of the penetrator into the piece being tested.

As can be readily understood, there is a rate of movement of the penetrator, and that rate of movement depends upon the material being tested as well as the penetrator and other factors. The rate of application of the penetrator to the piece being tested is determined by measuring the number of pulses per unit time generated by the encoder 54. A rate comparison is established in box 208, and that rate comparison is to indicate that the major load is finished being applied to the workpiece because the rate of application of the load to the workpiece is decreasing. Any such rate may be selected, and an appropriate number of counts per unit time can be selected to indicate the termination of the application of the major load. So long as that count has not yet been reached, or in other words as long as the count is greater than that number, no indication will be provided and a continuing sensing of the rate of application of the load to the piece being tested will continue. Once it is determined that the rate is equal to or less than that preset in box 208, then the major load ceases to be applied to the piece being tested. Of course, that moment is not instantaneous, and a dwell time is utilized related to the material being tested as well as to the certain ASTM standards. After the passage of the dwell time, the motor 62 is actuated through the energization of motor switch 64, and that begins to remove the major load from the piece being tested.

Again, the encoder 54 is utilized to determine the rate of removal or movement of the penetrator out of the workpiece, and here again, when that rate of movement is determined by the number of pulses produced by the encoder to be less than a preset amount, it will be determined that the test is completed and that the penetrator has moved from the workpiece at the preset rate. At this point, a measurement of the hardness of the material can be made, but because of the mechanical operations employed, a certain recovery time is preset according to the ASTM standards. After the passage of that recovery time has been identified by the recovery time box 210, a display of the hardness of the material will be shown in window 80. That display is identified in FIG. 4 as Item 212.

One of the other aspects of the present invention relates to the ability to standardize the rate of application of the major load to the piece being tested in order to ensure reliability and consistency from machine to machine. In particular, and as related to operation of the encoder 54, when the major load begins to be applied to the piece being tested, a pulse count is generated as at 214 in CPU 30, and that count pulse is generated according to a preset unit time. The count pulse begins after the passage of a certain preset time which relates to the piece being tested as well as the amount of major load being applied. For example, one could select a quarter or half of one second of time passage before beginning the unit count for the rate of application of the major load to the workpice being tested. Once that standard is set, each successive machine will be adjusted to be able to provide the same standard rate of application of load to the workpiece being tested.

In further reference to FIG. 4, the tester will be tested to determine whether or not the rate of the application of the major load is approximately equal to the preset, predetermined rate. In particular, the CPU 30 includes means 216 to determine the rate of application of the major load to the workpiece, and during that period, a switch 218 is activated to display in window 80 of FIG. 13, the rate of application of the major load to the workpiece. If that display is within the preset range, then the tester meets the consistency standards in the specification. In addition, such a comparison may be automatically built into the CPU 30 such that a rate of application of the major load to the workpiece can be preset, and a comparison of the presently tested machine with that preset standard can be made, so that the display need merely indicate that the machine is approved or not approved as falling within that preset standard.

Although the device has been described as being operated by the manual rotation of the capstan to raise the platform and workpiece, automatic means could be employed to automatically raise the capstan in order to apply the minor load. Thus, even further human error can be avoided, and there is further substantial assurance that the automatic application of the minor load will be according to preset standards because there is little likelihood that reversal of the movement of the elevating screw will take place as the minor load is being applied to the workpiece.

It can be understood that the above-described system utilizing a read encoder substantially eliminates human operator error in trying to sense when the major and minor loads are and should be applied or the measurements have or should be finished. Additionally, by determining and standardizing the rate of application of the major load, uniformity from machine to machine can easily be established.

The user may have the ability to vary the rate of application of load, but if that is done, the reliability of the machine can be impaired. On the other hand, CPU 30 can also preset the standard application rate so that the user can determine whether or not the machine is operating within the preset standard as identified by the original manufacturer. If the rate of application of the major load to a test block is not within the standard as preset and stored within the CPU, this can be displayed on display 80, and an adjustment can be made to adjust the rate of application of the major load.

Figure 5:
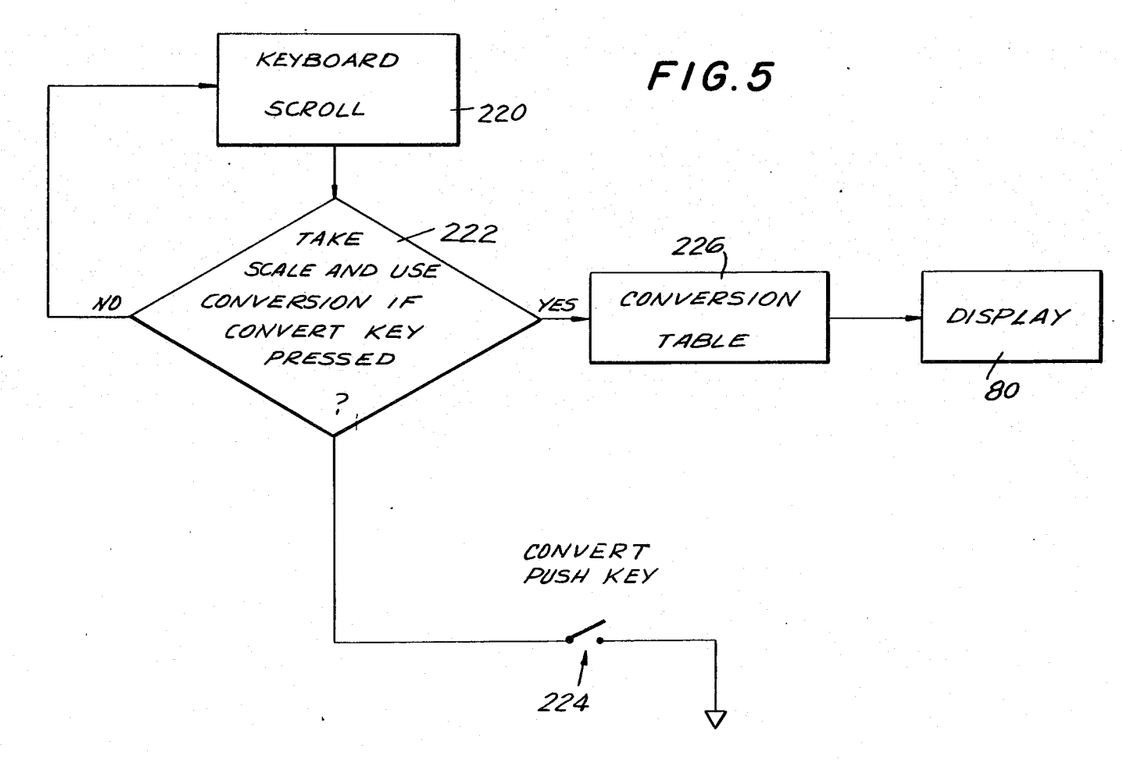
FIG. 5 is a flow chart illustrating the conversion from one scale to another of the tester.

FIG. 5 illustrates the flow chart of another of the features of this invention. In particular, and as described before, often a measurement is made according to one scale, while it is important that other scales be utilized for displaying the hardness of the material being tested. Generally, such scales are identified in conversion charts, and these conversion charts include a number of scales such as the C, A, D, 15-N, 30-N, 45-N as well as others. These tables each contain corresponding hardness readings relating to the scale being chosen. It may be desirable to test the workpiece in one scale, such as the C, yet be able to provide a hardness reading in another scale. In accordance with the features of this invention, the scales and corresponding related hardness measurements are stored within CPU 30.

The conversion scroll key 92 FIG. 13 is activated, and each respective scale is identified in window 94. This is energized after a measurement has already been made in one scale which had been preselected in the test by actuating the test scale scroll 90. After the test is completed, the conversion scroll is energized, and when the other desired scale is reached, the approximate conversion key 96 is activated. That scale conversion then causes the reading in the newly selected scale to be displayed in window 80, and in this fashion, the operator may easily derive hardness readings in different scales without having to resort to separate tables or having to separately manipulate different scale readings or hardness levels in order to adjust and find appropriate conversion data.

FIG. 5 illustrates the keyboard scroll 220 being energized to scroll the tables through window 94. The scale and conversion table is then activated by entering the CPU as per block 222, and if the convert pushbutton 224 (96) is energized, the conversion table 226 will be activated to produce the converted data on the display 80.

Figure 6:
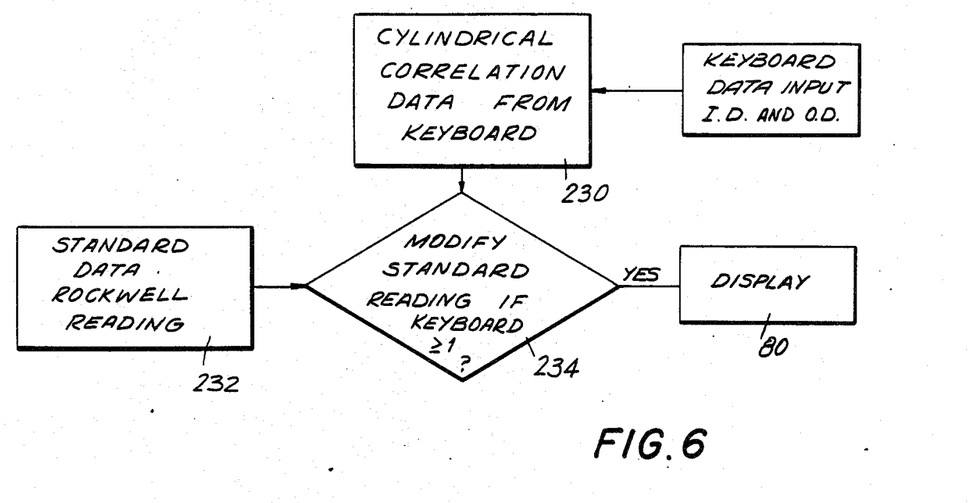
FIG. 6 is a flow chart illustrating the correction of the reading according to the shape of the material being tested.

As another aspect of the invention, and as illustrated in the flow chart of FIG. 6, certain measurements which are made on a flat workpiece need to be corrected for a cylindrical workpiece. In particular, cylindrical correction data is entered into CPU 30 as identified in block 230. The reading according to the standard hardness test is identified in 232, and a modification of the standard data according to cylindrical correlation data is achieved in modifier block 234 to produce a display as in window 80 which would be the modified or corrected display. Referring to FIG. 13, the cylindrical correction data is entered through the keyboard and the appropriate keys 122, 124 and 126 as well as the numerical keys. Once the size of the piece as well as the inside and outside diameters is entered, the modification can take place. Display 80 not only displays the corrected information but also displays that the displayed hardness is the corrected number rather than the standard number which originally was generated during the conventional hardness test.

Figure 7:
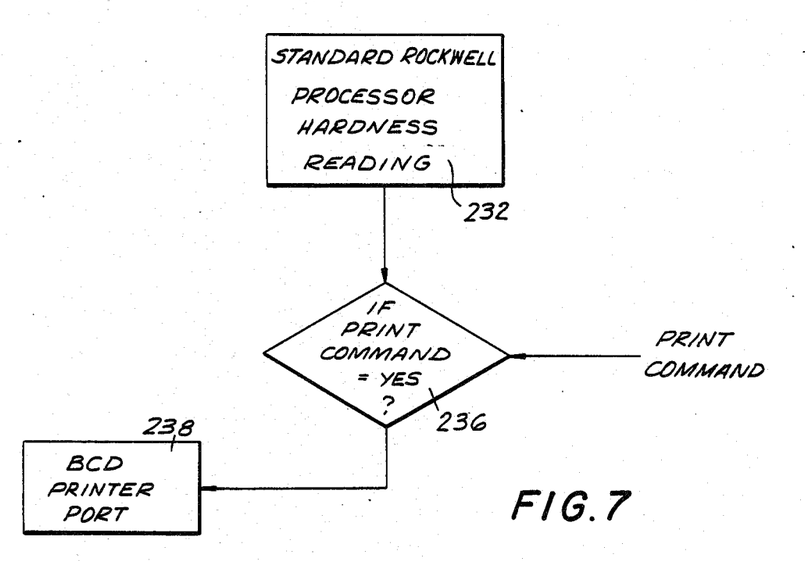
FIG. 7 is a flow chart illustrating the operation of the printer controlled by this tester.

FIG. 7 is a flow chart of the operation of this system in which a printer 70 is energized to print the data generated during the test. In particular, the hardness reading is generated as per the standard above-described process and is identified by numeral 232 which is similar to that numeral in FIG. 6. That information is supplied to a box identified as in print command 236 FIG. 7, and if a print command is entered into box 236, a print will be generated to activate the BCD printer port 238 such that the printer will print the desired information.

As described above, one of the problems with the prior art apparatus is the lack of multi-sensory direction to the operator. CPU-30 is identified in FIG. 8 as including an executive program, and CPU-30 includes ports and terminals to which a CRT interface 242 may be connected. The operative CRT interface 242 can be connected to a standard monitor 244, and suitable alpha-numeric data can be supplied from the CPU 30 through the interface 242 to monitor 244. Additionally, a voice synthesizer 246 may be employed and connected to a suitable port terminal of CPU-30. The voice synthesizer can activate a speaker 248, such that suitable alpha-numeric data can be keyed through the voice synthesizer to produce an oral display of desired information. The utilization of this will be more fully described later with regard to the repeated measurement of certain pieces as well as the measurement and comparison with certain ASTM standards.

Figure 8:
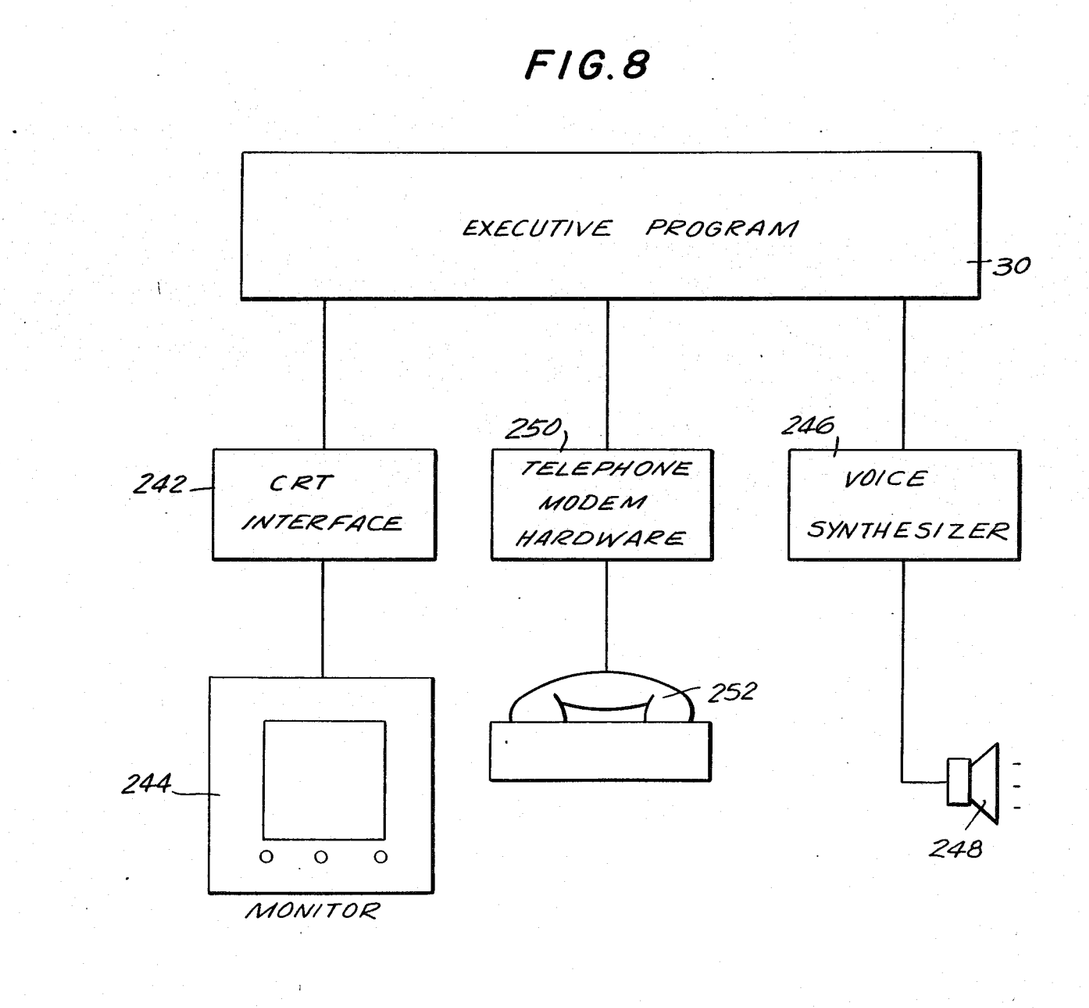
FIG. 8 is a block diagram of the connection of a voice synthesizer, telephone modem and CRT display to this apparatus.

CPU unit 30 also includes a modem terminal to which a telephone modem 250 may be connected, the output of which is connected to a standard telephone 252. It may be desirable to remotely test the testers in the field, and in order to ensure that the testers meet the most current testing criteria, the telephone modem may be employed. This modem could be interconnected with a central processing unit at the original manufacturer, and new information relating to new standards, updates, conversion charts and other information relating to information stored in the memory of the CPU could merely be transmitted from the hardness tester manufacturer to the telephone modem through the CPU to keep each tester current.

Figure 9:
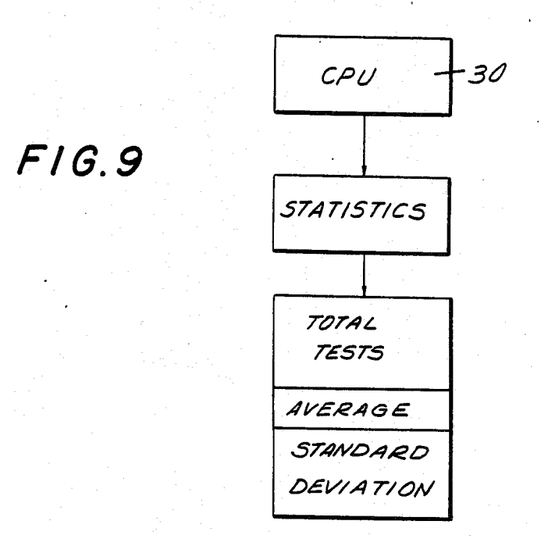
FIG. 9 is a block diagram of an aspect of this invention in which statistical data relating to certain measurements is employed.

As described above, one of the other problems with the prior devices is the difficulty of correlating the measurements over a period of time. In particular, the CPU 30 (FIG. 9) includes memory to store information related to the measurement processes including the day, time, type of workpiece, test result and other related data. In particular, a user of a machine may be able to determine the general quality of the tested materials over a period of time, and they also may be able to determine standard deviations and other statistical values.

Figure 10:
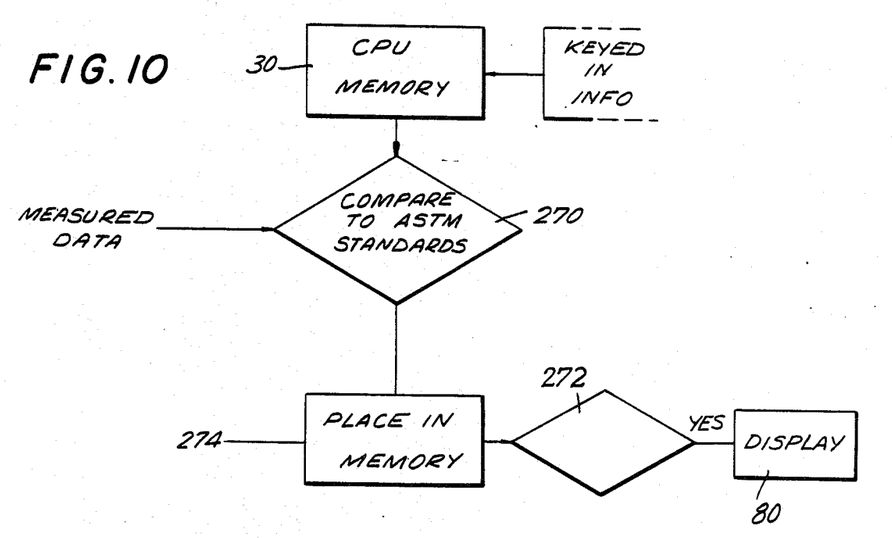
FIG. 10 is a block diagram of the entry and control of the tester according to preset ASTM standards utilizing test blocks.

One of the important aspects of this invention is the ability to determine whether or not the machine is properly operating within certain ASTM specifications. This is accomplished by utilizing the present apparatus. FIG. 10 is a flow diagram of this process. In particular, the memory of CPU 30 stores ASTM test data related to certain test blocks. These test blocks are used in the place of the workpiece which has been previously identified in order to determine whether or not the tester is operating according to standard procedures. The data relating to the type of test block is keyed into the system by using the numerical and function keys. As the tests are run, a comparison in block 270 is made of the stored ASTM data to the measured data.

The output of the comparison of the tables accomplished in box 270 is then stored in the memory of CPU 30 acording to flow step 272, and if the measurements and comparison of the test procedures are in compliance with the ASTM standards, a Yes signal is developed as in block 274 and the display 80 indicates that the tester met the ASTM standards.

Figure 11:
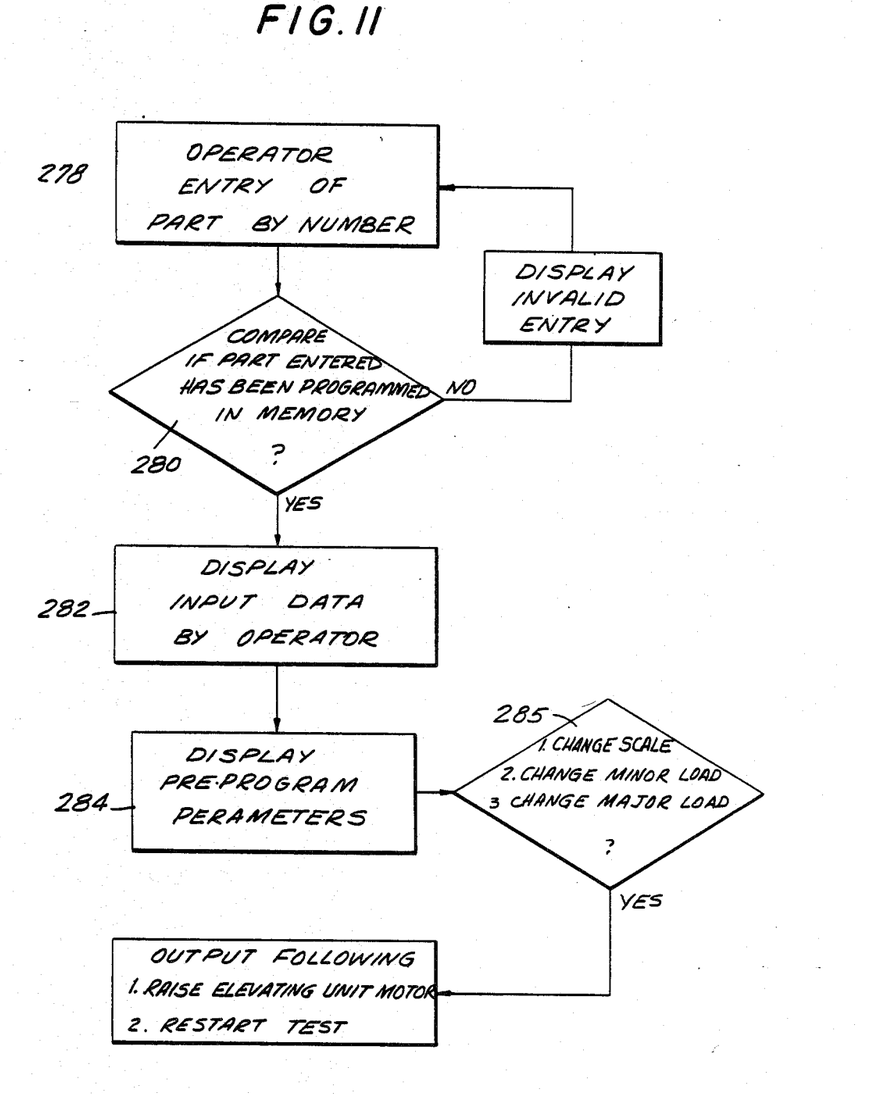
FIG. 11 is a block diagram illustrating the operation of this invention in which certain regularly tested parts are identified and the operating procedure and standards relating to those parts is visually and/or orally displayed.

FIG. 11 is yet another flow diagram of another feature of this invention. In particular, some users find that they repeatedly conduct tests on the same part. That part may have a standard number, and rather than having the operator regularly consult a separate chart to determine the operating parameters and procedures for that part, CPU 30 may store the data according to the part number being tested. The operator merely needs to key in the part number by identification as in block 278, and the CPU can orally and visually present the standards and procedures to be followed by the tester. The part number entered is compared to see if it is in the memory of CPU 30 as in block 280. If there is an invalid entry, the process terminates. On the other hand, if there is a valid entry, the input data to be used is displayed for the operated in block 282. Additionally, the operating parameters are displayed in block 284. Depending on the displays in 282 and 284 (or automatic entries where applicable) the scales, loads, etc. are set in automatically to operate the test. Additionally, the CPU could automatically control the operation and test run on the workpiece in order to determine whether or not that workpiece falls within the standards set according to that information previously stored in the CPU.

The above invention has been described with regard to certain preferred embodiments. This invention presents a fully automatic relatively foolproof, consistent, reliable and accurate hardness tester in which tests from machine to machine can be consistent and in which the possibility of human error is largely eliminated. The ability to easily convert from table to table, scale to scale as well as to adjust and correct for certain factors such as the cylindrical size and shape being tested is a significant improvement over the prior art. Additionally, the ability to ensure that the tester falls consistently within certain ASTM standards by using test blocks to produce results which are then compared with the stored ASTM standards in the CPU 30 also provides improved significant improvement over prior art. Still further, the ability to continue to update the CPU information according to revised data and to provide transmission to a central location provides a significant improvement over the prior art.

The use of simultaneous visual and oral instructions as well as display information to assist the operator in the performance of the tests also represents an improvement in this field.

The above embodiments have been described as preferred and modifications, changes and alterations may be employed by those skilled in the art without departing from the spirit of scope of this invention.

What is claimed is:

1. A machine for testing the hardness of a material according to a predetermined scale, said machine comprising
    a platform on which a workpiece to be tested is carried,
    an elevating unit for elevating the platform,
    a penetrator penetrating the workpiece as the platform is raised toward the penetrator to apply a minor load to the workpiece,
    means to apply a major load to the workpiece and moving the penetrator further into the workpiece,
    means to remove the major load from the workpiece,
    means to determine the hardness of the workpiece by comparing the relative depths of penetration of the penetrator under conditions of the application of the major and minor loads,
    an improvement comprising
    means to generate a series of pulses representative of the relative movement between said penetrator and said workpiece, said means to generate a series of pulses comprising means to indicate the relative direction of movement between said penetrator and workpiece while the workpiece is being moved,
    means to sense when the direction of relative movement between said penetrator and workpiece is reversed while said minor load is being applied,
    and means to abort the operation of the machine when there is a reversal of direction of said movement.

2. A machine for testing the hardness of a material according to claim 1, further comprising display means to display when there is a reversal of direction and a termination of the operation of the machine.

3. A machine for testing the hardness of a material according to a predetermined scale, said machine comprising
    a platform on which a workpiece to be tested is carried,
    an elevating unit for elevating the platform,
    a penetrator penetrating the workpiece as the platform is raised toward the penetrator to apply a minor load to the workpiece,
    means to apply a major load to the workpiece and moving the penetrator further into the workpiece,
    means to remove the major load from the workpiece,
    means to determine the hardness of the workpiece, comparing the relative depths of penetration of the penetrator under conditions of the application of the major and minor loads,
    an improvement comprising
    means to generate a series of pulses representative of the relative movement between said penetrator and said workpiece,
    and means to sense the rate of application of the penetrator to the workpiece.

4. A machine for testing the hardness of a material according to claim 3,
    further comprising means to terminate application of the penetrator when said rate of application of said major load falls below a predetermined level.

5. A machine for testing the hardness of a material according to claim 3, further comprising means to standardize the rate of application of the major load to a standard workpiece comprising means to count said series of pulses per unit time to generate a standard for said rate of application, said standard being applied to the rate of application of the major load for other machines for testing the hardness of materials.

6. A machine for testing the hardness of a material according to claim 5, further comprising means to sense when said major load begins to be applied, means to delay beginning the count of said pulses and means to count said pulses after said delay.

7. A machine for testing the hardness of a material according to claim 3, further comprising means to remove said major load from said workpiece by moving said penetrator out of contact with said workpiece and means to sense the rate at which said penetrator is moving from said workpiece and to terminate the hardness measurement procedure when the rate of removal of the major load is equal to a predetermined rate.

8. A machine for testing the hardness of a material according to claim 7, further comprising means to determine the hardness of the workpiece by counting the difference between the number of pulses generated during application of the minor load and during the removal of the major load.

9. A machine for testing the hardness of a material according to claim 8, further comprising means to store a plurality of measurement scales, means responsive to the measured hardness to display an amount representative of the hardness in one scale of measurement and means to display that scale of measurement.

10. A machine for testing the hardness of a material according to claim 9, further comprising means connected to said plurality of scales and said measured hardness value to automatically display the hardness in any of said plurality of measurement scales.

11. A machine for testing the hardness of a material according to claim 10, further comprising means to scroll said plurality of measurement scales to select the scale which the hardness is to be displayed.

12. A machine for testing the hardness of a material according to claim 8, further comprising means to store a plurality of correction factors relating to the shape of a cylindrical workpiece, said factors including the inside and outside diameters of said workpiece and means to convert the measured hardness to a corrected hardness, means to supply the measured hardness and said plurality of correction factors to said means to convert and display means connected to said means to convert to display said corrected hardness value and the identity of a corrected value.

* * * * *